United States Patent
Oduro et al.

(10) Patent No.: US 10,501,679 B2
(45) Date of Patent: Dec. 10, 2019

(54) IRON SULFIDE DISSOLVER

(71) Applicant: Saudi Arabian Oil Company, Dhahran (SA)

(72) Inventors: Harry Daniel Oduro, Dhahran (SA); Mohammed Khaldi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 113 days.

(21) Appl. No.: 15/885,207

(22) Filed: Jan. 31, 2018

(65) Prior Publication Data

US 2019/0233711 A1 Aug. 1, 2019

(51) Int. Cl.

| | |
|---|---|
| C09K 8/532 | (2006.01) |
| C07C 63/06 | (2006.01) |
| C07C 53/02 | (2006.01) |
| C01G 9/00 | (2006.01) |
| C01G 37/00 | (2006.01) |
| C07C 53/08 | (2006.01) |
| C01G 49/12 | (2006.01) |
| C07C 321/14 | (2006.01) |

(52) U.S. Cl.
CPC ............... *C09K 8/532* (2013.01); *C01G 9/00* (2013.01); *C01G 37/00* (2013.01); *C01G 49/12* (2013.01); *C07C 53/02* (2013.01); *C07C 53/08* (2013.01); *C07C 63/06* (2013.01); *C07C 321/14* (2013.01); *C09K 2208/20* (2013.01)

(58) Field of Classification Search
CPC ...... C09K 8/52; C09K 8/532; C09K 2208/20; C07C 53/02; C07C 53/08; C01G 9/00; C01G 37/00
See application file for complete search history.

(56) References Cited

U.S. PATENT DOCUMENTS

| | | |
|---|---|---|
| 3,794,523 A | 3/1974 | Thompson |
| 4,220,550 A | 11/1980 | Frenier et al. |
| 4,276,185 A | 6/1981 | Martin |
| 4,289,639 A | 11/1981 | Buske |
| 4,381,950 A | 5/1983 | Lawson |
| 7,611,588 B2 | 11/2009 | Peitersen et al. |
| 8,039,422 B1 | 10/2011 | Al-Zahrani |
| 2003/0062316 A1 | 4/2003 | Mattox et al. |
| 2007/0282131 A1 | 12/2007 | Stauffer |
| 2011/0152153 A1 | 6/2011 | Trahan et al. |

FOREIGN PATENT DOCUMENTS

JP 2000219673 8/2000

OTHER PUBLICATIONS

International Search Report and Written Opinion issued in International Application No. PCT/US2019/015548 dated Apr. 12, 2019, 15 pages.
Nasr-El-Din et al., "Iron Sulfide Scale: Formation, Removal and Prevention," International Symposium on Oilfield Scale, Jan. 1, 2001, 13 pages.
Leal et al., "A Systematic Approach to Remove Iron Sulphide Scale: A Case History," SPE Middle East Oil and Gas Show and Conference, Jan. 1, 2007, 10 pages.

*Primary Examiner* — Aiqun Li
(74) *Attorney, Agent, or Firm* — Fish & Richardson P.C.

(57) ABSTRACT

An aqueous iron sulfide dissolver including zinc, chromium, a methoxybenzoic acid, formic acid, acetic acid, and hydrochloric acid. The iron sulfide dissolver is made by combining these components, and dissolves compounds including iron sulfide upon contact. Evolved hydrogen sulfide reacts with the methoxybenzoic acid to yield solubilized methanethiol as an intermediate product, which is further oxidized to yield dissolved dimethyl disulfide.

20 Claims, 1 Drawing Sheet

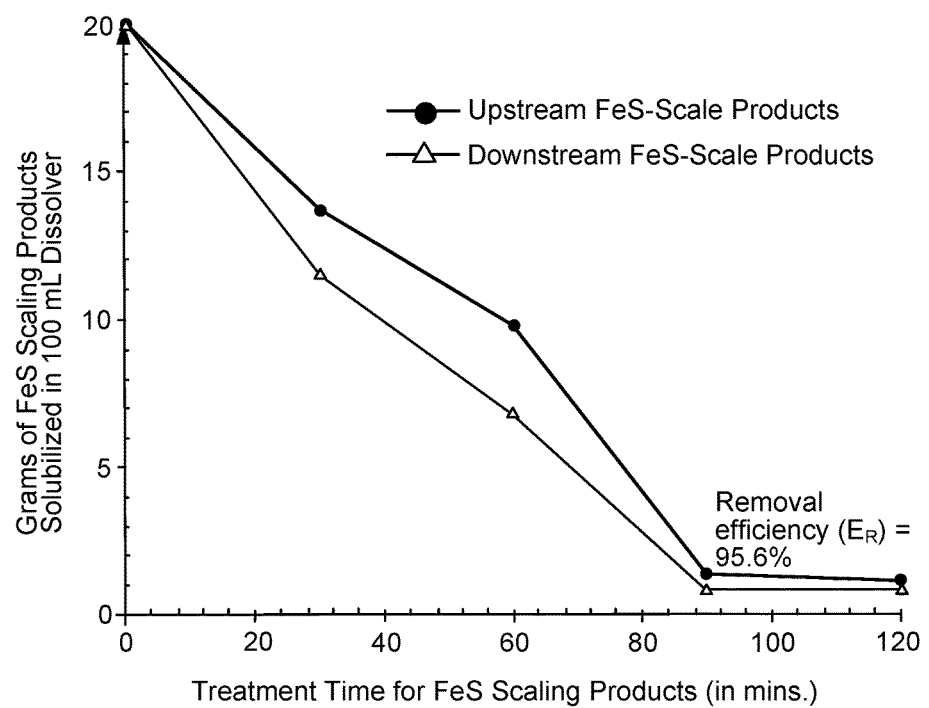

IRON SULFIDE DISSOLVER

TECHNICAL FIELD

This disclosure relates to an iron sulfide dissolver suitable for controlling large scale iron sulfide deposition and scaling in oil and gas fields.

BACKGROUND

The formation and deposition of iron sulfide scaling products inhibits or blocks hydrocarbon migration pathways, ultimately reducing production, and causes severe corrosion and equipment damage to both upstream and downstream facilities. As used here, "iron sulfide" and "iron sulfides" refers to compounds including iron and sulfur in various proportions, such as mackinawite (FeS), pyrrhotite ($Fe_{(1-x)}S$), greigite ($Fe_3S_4$), marcasite ($FeS_2$ polymorph), and pyrite ($FeS_2$). Iron sulfide scaling in sour petroleum systems is often ignored because of the difficulty in preventing its formation through nucleation, aggregation, and large scale build-up of iron sulfide minerals according to the transformation shown in Reaction (1).

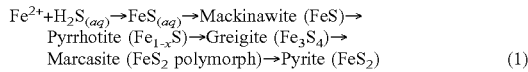  (1)

Scaling removal techniques typically used to restore reservoir productivity in oil and gas fields include conventional chemical and mechanical techniques. However, the mechanical cleaning techniques are very expensive, entail laborious processes, and do not adequately remove most of the stable iron sulfide scaling products (such as $Fe_3S_{4(greigite)}$, $FeS_{2(marcasite)}$ and $FeS_{2(pyrite)}$) that are directly in contact with downhole wellheads and pipelines. Moreover, some cleaning processes can cause abrasive wear to production metal coatings without restoring the permeability that has been lost in downhole producing zones.

Aqueous acid chemical removal methods have been recognized to reduce some iron sufide scaling products (such as $FeS_{(mackinawite)}$ and $Fe_{(1-x)}S_{(pyrrhotite)}$) in the petroleum industry. However, laboratory and pilot plant data show that upon contact with iron sulfide scaling products, these acidic solvents release hydrogen sulfide ($H_2S$), free-floating iron sulfides, and sulfur intermediate species that undergo oxidation into sulfate and other components that are less readily dissolved by acidic solutions. The released hydrogen sulfide is hazardous and poses a health threat to oilfield workers, and the free-floating iron sulfides lead to additional scaling, formation damage, and corrosion problems in oil and gas fields. In addition, the oxidized sulfur intermediates are much less readily dissolved by acidic solutions than the iron sulfides.

SUMMARY

In a first general aspect, an aqueous iron sulfide dissolver includes zinc, chromium, a methoxybenzoic acid, formic acid, acetic acid, and hydrochloric acid, where acid refers to the acid as well as its conjugate base.

In a second general aspect, making an aqueous iron sulfide dissolver for dissolving iron sulfide includes combining zinc, chromium, a methoxybenzoic acid, formic acid, acetic acid, and hydrochloric acid to yield the aqueous iron sulfide dissolver.

In a third general aspect, dissolving an iron sulfide includes contacting an iron sulfide with an aqueous iron sulfide dissolver including zinc, chromium, a methoxybenzoic acid, formic acid, acetic acid, and hydrochloric acid to dissolve the iron sulfide; reacting evolved hydrogen sulfide with the methoxybenzoic acid to yield methanethiol; and dimerizing the methanethiol to yield dimethyl disulfide in solution.

Implementations of the first, second, and third general aspects may include one or more of the following features.

The methoxybenzoic acid may include a trimethoxy benzoic acid, a dimethoxy benzoic acid, or both. On example of a trimethoxybenzoic acid is 3,4,5-trimethoxybenzoic acid. One example of a dimethoxybenzoic acid is syringic acid (3,5-dimethoxy-4-hydroxybenzoic acid). The zinc may be in the form of zinc metal. The chromium may be in the form of a chromium salt.

A molar ratio of the zinc to the chromium is in a range of 1 to 3, in a range of 1.5 to 2.5, or about 2. A molar ratio of the formic acid to the chromium is in a range of 3.5 to 5.5, in a range of 4.5 to 5.5, or in a range of 5 to 5.5. A molar ratio of the acetic acid to the chromium is in a range of 2.5 to 4.5, a range of 3.5 to 4.5, or about 4. A molar of the hydrochloric acid to the chromium is in a range of 1 to 3, in a range of 1.5 to 2.5, or in a range of 2 to 2.5. A molar ratio of the methoxybenzoic acid to the chromium is in a range of 1.1 to 2.5 or in a range of 1.5 to 2.

Implementations of the third general aspect may include one or more of the following features.

The aqueous iron sulfide dissolver may be introduced into a wellbore, and contacting the iron sulfide with the aqueous iron sulfide dissolver may occur downhole. Dissolving an iron sulfide may further include removing the dimethyl disulfide from the solution.

The iron sulfide dissolver can be used to treat unwanted iron sulfide scaling products that inhibit or block hydrocarbon migration pathways and ultimately reduce production in oilfields. The dissolver also removes hydrogen sulfide ($H_2S$) products during the treatment process, and can be used to control large scale deposition of iron sulfides and scaling related problems in oil and gas fields. The dissolver is a strong reducing agent suitable for removing iron sulfides from sedimentary carbonate and sulfur-bearing reservoirs. The dissolver is suitable for removing downhole and pipeline iron sulfide material. The iron sulfide dissolver is thermally stable during downhole and pipeline cleaning operations, which means that the iron sulfide dissolver maintains effectiveness under the temperature and pressure conditions during treatment.

The details of one or more implementations of the subject matter described in this specification are set forth in the following description. Other features, aspects, and advantages of the subject matter will become apparent from the description, the drawings, and the claims.

BRIEF DESCRIPTION OF THE DRAWINGS

FIG. 1 shows dissolution of upstream and downstream iron sulfide samples in an iron sulfide dissolver over time.

DETAILED DESCRIPTION

An aqueous iron dissolver is formed by dissolving a chromium (III) salt and zinc metal in an acidic solution to yield a dark green chromium (III) solution, and reducing the chromium (III) to chromium (II) as shown in Reaction (2) in the absence of oxygen to yield a bright blue chromium (II) solution.

  (2)

Chromium (III) chloride hexahydrate (CrCl$_3$.6H$_2$O) is an example of a suitable chromium salt. The zinc metal is typically a granulated zinc metal. Suitable particle sizes include 20-25 mesh. The acidic solution is typically a mixture of formic acid (HCOOH), acetic acid (CH$_3$COOH), and hydrochloric acid (HCl).

The aqueous iron sulfide dissolver can include a methoxybenzoic acid. In some embodiments, a methoxybenzoic acid is combined with the chromium (II) solution. The methoxybenzoic acid imparts stability and aids in removal of hydrogen sulfide produced during downhole and pipeline dissolution and removal operations. Suitable methoxybenzoic acids include dimethoxybenzoic acid (such as 3,5-dimethoxy-4-hydroxybenzoic acid or syringic acid) and trimethoxybenzoic acid (such as 3,4,5-trimethoxybenzoic acid or trimethylgallic acid). A solvent may be combined with the methoxybenzoic acid before adding the methoxybenzoic acid to chromium (II) solution. Suitable solvents include ethanol, propanol, butanol, pentanol, hexanol, and other polar organic solvents (such as solvents having one or more —OH, —NH$_2$ or —CO$_2$H groups) with a polarity exceeding that of ethanol, a boiling point exceeding that of ethanol, or both. In one example, 2 molar (M) to 2.5M methoxybenzoic acid in ethanol is added to the chromium (II) solution.

The aqueous iron sulfide dissolver includes zinc, chromium, methoxybenzoic acid (such as 3,4,5-trimethoxybenzoic acid) and its conjugate base (3,4,5-trimethoxybenzoate), formic acid and its conjugate base (formate), acetic acid and its conjugate base (acetate), and hydrochloric acid and its conjugate base (chloride). As used here for purposes of concentration, the concentration of an acid in the aqueous iron sulfide dissolver is understood to be the sum of the concentration of the acid and the concentration of its conjugate base. A molar ratio of the zinc to the chromium is typically in a range of 1 to 3 or a range of 1.5 to 2.5. In some cases, the molar ratio of the zinc to the chromium is about 2. A molar ratio of the formic acid to the chromium is typically in a range of 3.5 to 5.5, a range of 4.5 to 5.5, or a range of 5 to 5.5. A molar ratio of the acetic acid to the chromium is typically in a range of 2.5 to 4.5, a range of 3.5 to 4.5, or a range of 5 to 5.5. A molar ratio of the hydrochloric acid to the chromium is typically in a range of 1 to 3, a range of 1.5 to 2.5, or a range of 2 to 2.5. A molar ratio of the methoxybenzoic acid to the chromium is typically in a range of 1.1 to 2.5 or 1.5 to 2. In one example, an aqueous iron sulfide dissolver has the following composition: 1.1M to 1.5M chromium, 2.2M to 3M zinc, 2.4M hydrochloric acid, 5.9M formic acid, 4.4M acetic acid, and 2.0M methoxybenzoic acid.

Dissolving iron sulfide, such as iron sulfide scaling and formation products, includes contacting the iron sulfide with the aqueous iron sulfide dissolver to oxidize iron (II), yielding iron (III) and hydrogen sulfide as shown in Reaction (3).

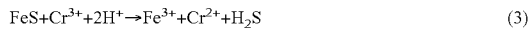

$$FeS + Cr^{3+} + 2H^+ \rightarrow Fe^{3+} + Cr^{2+} + H_2S \qquad (3)$$

Other iron sulfides are similarly dissolved. In particular, the iron sulfide dissolver mitigates most or all forms of iron sulfide scaling, corrosion related metal sulfides, and formation damage in oil and gas fields. The iron sulfide dissolver can also remove other metal sulfides and oxides including galena (PbS), magnetite (Fe$_3$O$_4$), hematite (Fe$_2$O$_3$), and iron-oxyhydroxide (FeOOH) scaling in conventional and unconventional hydrocarbon wells and pipelines. Suitable treatment temperatures are between 70 degrees Celsius (° C.) and 110° C., or between 70° C. and 80° C. or 100° C. and 110° C.

The hydrogen sulfide produced or evolved during the dissolution of iron sulfides in Reaction (3) is methylated by the alkoxybenzoic acid in the aqueous iron dissolver. When the methoxybenzoic acid is 3,4,5-trimethoxybenzoic acid, methylation of the hydrogen sulfide occurs in solution as shown in Reaction (4).

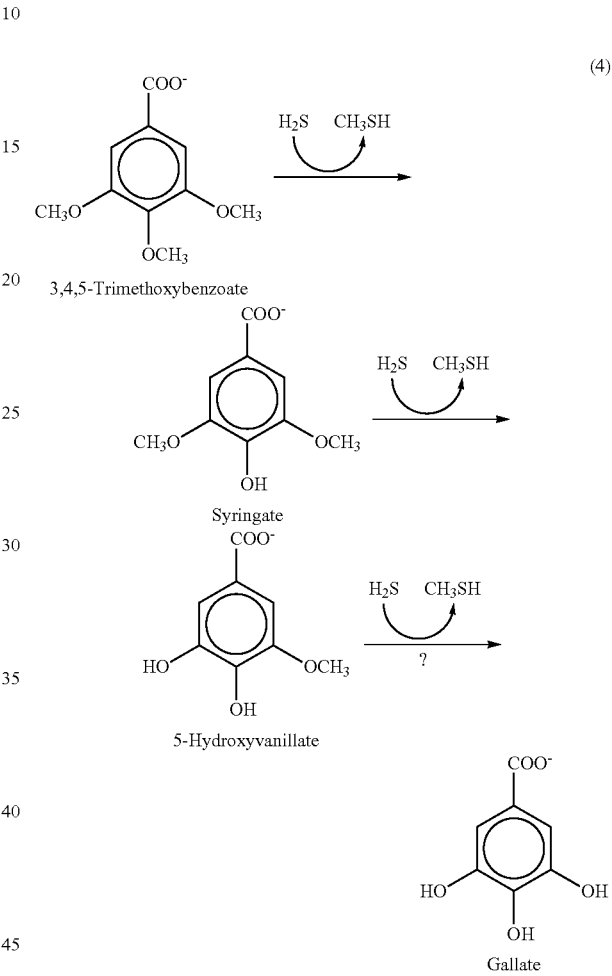

As shown in Reaction (4), hydrogen sulfide reacts with 3,4,5-trimethoxybenzoate to yield methanethiol (CH$_3$SH) and syringate, reacts with syringate to yield methanethiol and 5-hydroxyvanillate, and also reacts with 5-hydroxyvanillate to yield methanethiol and gallate.

The methanethiol may undergo solution phase dimerization in the presence of atmospheric oxygen to form dimethyl disulfide, as shown in Reaction (5).

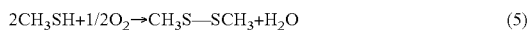

$$2CH_3SH + 1/2O_2 \rightarrow CH_3S-SCH_3 + H_2O \qquad (5)$$

The dimethyl disulfide is soluble in aqueous solution. The solubilized iron, chromium, and other trace metal components, together with soluble dimethyl disulfide components can be recovered by pumping from downhole to the surface for further storage and treatment.

Iron sulfide removal efficiency ($E_R$) can be calculated as [100−(dry weight of iron sulfide sample after treatment/dry weight of the iron sulfide sample before treatment)]×100. Removal efficiency is typically at least 95 percent (%). Quantifying the removal efficiency allows optimization of the proportion or ratio of solvent to iron sulfide samples, optimization of temperature and pressure of the dissolution process, time required for the chemical treatment of different iron sulfides, and recoverable hydrogen sulfide ($R_{H2S}$) present in the spent acid or residual dissolver. Recoverable hydrogen sulfide (that is, hydrogen sulfide that has not reacted to yield soluble methanethiol or dimethyl disulfide) can be calculated by a gravimetric silver sulfide method, with the mass of hydrogen sulfide calculated as shown in Equation (6).

$$\text{Recoverable } H_2S \text{ (g)}=g \text{ } Ag_2S \text{ recovered} \times (1 \text{ mole } Ag_2S/247.8 \text{ g}) \times (1 \text{ mole } H_2S/1 \text{ mole } Ag_2S) \times (34.1 \text{ g } H_2S/1 \text{ mole } H_2S) \quad (6)$$

EXAMPLES

To prepare the iron dissolver, 1.1 moles of chromium (III) hexahydrate ($CrCl_3.6H_2O$ available from Acros, 98% purity) was combined with 2.3 moles of granulated zinc metal (20 mesh, available from JT Baker) to yield a solid mixture. The solid mixture was combined with an aqueous mixture of 2.4 moles hydrochloric acid, 5.9 moles formic acid, and 4.4 moles acetic acid. The mixture was stirred at room temperature for 3 hours under constant flow of ultra-high purity nitrogen until the solution turned from a dark green chromium (III) solution to a bright blue chromium (II) solution. A 2M solution of syringic acid (3,5-dimethoxy-4-hydroxybenzoic acid, available from Sigma) in ethanol (40 wt % syringic acid) was prepared and added to the chromium (II) solution.

Batch confirmatory tests were performed on pipeline and downhole scale products from oilfields, demonstrating convenient application of the iron sulfide dissolver for the removal of large quantities of scaling products. Surface morphology by environmental scanning electron microscopy (ESEM) and mineral characterization by X-ray diffraction (XRD) patterns were characterized for (1) upstream corrosion scaling products composed of solid akaganeite (FeOOH), goethite (FeOOH), and iron sulfides with particle sizes in a range of 226.1 micrometers (μm) to 317 μm and (2) downstream pipeline black powder products composed of sulfur ($S_8$), pyrrhotite ($Fe_{(1-x)}S$), pyrite ($FeS_2$), and magnetite ($Fe_3O_4$) with particle sizes ranging from 6.20 μm to 129.30 μm. The removal efficiency of the solids was experimentally determined in a stainless steel apparatus. In all experiments, 20 gram (g) solid samples were treated with 100 milliliter (mL) volume of the iron sulfide dissolver (prepared as described) and heated to 110° C. Within 1.5 hours of treatment, the iron scaling and black powder samples were dissolved without emission of hydrogen sulfide gas.

Overall results showed that the average removal efficiency ($E_R$(%)) for both upstream and downstream iron sulfide scale and formation damage products was 95.6% and increased with temperature (at constant pressure) in all cases.

Recoverable hydrogen sulfide was assessed by a gravimetric silver sulfide method through the following procedure. After iron sulfide sample treatment with the iron sulfide dissolver, the treated supernatant solution was filtered to remove any residual or undissolved iron sulfide. After filtration, 5.0 mL of 1.0M silver nitrate solution ($AgNO_3$) was added dropwise to the filtrate to convert dissolved hydrogen sulfide into silver sulfide ($Ag_2S$) precipitate according to Reaction (6).

$$2AgNO_{3(aq)} + H_2S_{(aq)} \rightarrow 2Ag_2S_{(S)} + 2HNO_{3(aq)} \quad (7)$$

The precipitated silver sulfide was filtered from the solution, rinsed twice with deionized water, and dried overnight in an oven at a temperature of 46° C. The dry silver sulfide was weighed on a microanalytical balance to yield the gravimetric weight or amount of $H_2S$ recovered from the supernatant acid treatment solution.

Laboratory experiments using the sulfide- and oxide-containing minerals mackinawite, pyrrhotite, marcasite, greigite, pyrite, galena, magnetite, and goethite (available from Ward's Natural Science, Rochester, N.Y.) having a particle size of about 500 μm were conducted. All experiments were performed by combining 1 gram of iron sulfide mineral with 5 mL of iron sulfide dissolver, followed by constant heating of the sample mixture on a heating mantle at a temperature between 96° C. and 103° C. for 3 hours at standard atmospheric pressure. Table 1 lists parameters for each sample, including initial and final sample weight, volume of iron dissolver, and treatment temperature, and as well as iron sulfide removal efficiency ($E_R$) and recoverable hydrogen sulfide ($R_{H2S}$). The removal efficiency for each sample exceeded 97%.

TABLE 1

Operating parameters and results for dissolution of iron sulfides

| Standard FeS Minerals | Initial weight of sample (g) | Volume of Iron Sulfide Dissolver (mL) | Final weight of FeS sample (g) | Removal Efficiency ($E_R$, %) | Recoverable $H_2S$ ($R_{H2S}$, grams) |
|---|---|---|---|---|---|
| $FeS_{(mackinawite)}$ | 1.0 | 5.0 | 0.011 | 98.9 | 0.06 |
| $Fe_{(1-x)}S_{(pyrrhotite)}$ | 1.0 | 5.0 | 0.017 | 98.3 | 0.04 |
| $Fe_3S_{4(Greigite)}$ | 1.0 | 5.0 | 0.023 | 97.7 | 0.11 |
| $FeS_{2(marcasite)}$ | 1.0 | 5.0 | 0.019 | 98.1 | 0.07 |
| $FeS_{2(pyrite)}$ | 1.0 | 5.0 | 0.021 | 97.9 | 0.21 |
| FeOOH | 1.0 | 5.0 | 0.003 | 99.7 | 0 |
| $Fe_3O_{4(magnetite)}$ | 1.0 | 5.0 | 0.005 | 99.5 | 0 |
| $PbS_{(galena)}$ | 1.0 | 5.0 | 0.008 | 99.2 | 0.04 |

Treatment of upstream and downstream oilfield iron sulfide scale samples was achieved by a dynamic analytical method in a stainless steel apparatus. In all experiments, 20 gram solid samples were treated with 100 mL of iron sulfide dissolver and heated to 110° C. Within one and half hours of treatment, the samples were dissolved ($E_R$ about 95%) with little or no emission of $H_2S$. Data from the dissolution of the upstream and downstream iron sulfide samples, assessed every 30 minutes, is listed in Table 2. FIG. 1 shows dissolution of the upstream and downstream iron sulfide samples over time.

TABLE 2

Dissolution of upstream and downstream iron sulfide samples over time

| Upstream FeS Products (grams in 100 mL) | Downstream FeS Products (grams in 100 mL) | FeS removal time (minutes) |
|---|---|---|
| 20.0 | 20.0 | 0 |
| 13.7 | 11.6 | 30 |
| 9.8 | 6.9 | 60 |
| 1.4 | 0.9 | 90 |
| 1.2 | 0.9 | 120 |

Thus, particular implementations of the subject matter have been described. Other implementations are within the scope of the claims.

What is claimed is:

1. An aqueous iron sulfide dissolver comprising:
   zinc;
   chromium;
   a methoxybenzoic acid, wherein "methoxybenzoic acid" refers to the methoxybenzoic acid and its conjugate base;
   formic acid, wherein "formic acid" refers to formic acid and its conjugate base;
   acetic acid, wherein "acetic acid" refers to acetic acid and its conjugate base; and
   hydrochloric acid, wherein "hydrochloric acid" refers to hydrochloric acid and its conjugate base.

2. The aqueous iron sulfide dissolver of claim 1, wherein the methoxybenzoic acid comprises a trimethoxybenzoic acid.

3. The aqueous iron sulfide dissolver of claim 2, wherein the trimethoxybenzoic acid comprises 3,4,5-trimethoxybenzoic acid.

4. The aqueous iron sulfide dissolver of claim 1, wherein the methoxybenzoic acid comprises a dimethoxybenzoic acid.

5. The aqueous iron sulfide dissolver of claim 4, wherein the dimethoxybenzoic acid comprises syringic acid (3,5-dimethoxy-4-hydroxybenzoic acid).

6. The aqueous iron sulfide dissolver of claim 1, wherein a molar ratio of the zinc to the chromium is in a range of 1 to 3.

7. The aqueous iron sulfide dissolver of claim 1, wherein the molar ratio of the zinc to the chromium is in a range of 1.5 to 2.5.

8. The aqueous iron sulfide dissolver of claim 1, wherein a molar ratio of the formic acid to the chromium is in a range of 3.5 to 5.5.

9. The aqueous iron sulfide dissolver of claim 1, wherein a molar ratio of the acetic acid to the chromium is in a range of 2.5 to 4.5.

10. The aqueous iron sulfide dissolver of claim 1, wherein a molar ratio of the hydrochloric acid to the chromium is in a range of 1 to 3.

11. The aqueous iron sulfide dissolver of claim 10, wherein the molar ratio of the hydrochloric acid to the chromium is in a range of 1.5 to 2.5.

12. The aqueous iron sulfide dissolver of claim 11, wherein the molar ratio of the hydrochloric acid to the chromium is in a range of 2 to 2.5.

13. The aqueous iron sulfide dissolver of claim 1, wherein a molar ratio of the methoxybenzoic acid to the chromium is in a range of 1.1 to 2.5.

14. The aqueous iron sulfide dissolver of claim 13, wherein the molar ratio of the methoxybenzoic acid to the chromium is in a range of 1.5 to 2.

15. A method of making an aqueous iron sulfide dissolver for dissolving iron sulfides, the method comprising:
    combining zinc, chromium, a methoxybenzoic acid, formic acid, acetic acid, and hydrochloric acid to yield the aqueous iron sulfide dissolver.

16. The method of claim 15, wherein the zinc is in the form of zinc metal.

17. The method of claim 15, wherein the chromium is in the form of a chromium salt.

18. A method of dissolving an iron sulfide, the method comprising:
    contacting an iron sulfide with an aqueous iron sulfide dissolver comprising zinc, chromium, a methoxybenzoic acid, formic acid, acetic acid, and hydrochloric acid to dissolve the iron sulfide;
    reacting evolved hydrogen sulfide with the methoxybenzoic acid to yield methanethiol; and
    dimerizing the methanethiol to yield dimethyl disulfide in solution.

19. The method of claim 18, further comprising introducing the aqueous iron sulfide dissolver into a wellbore, wherein contacting the iron sulfide with the aqueous iron sulfide dissolver occurs downhole.

20. The method of claim 18, further comprising removing the dimethyl disulfide from the solution.

* * * * *